(12) United States Patent
Al Askar

(10) Patent No.: US 11,992,239 B2
(45) Date of Patent: May 28, 2024

(54) PALATAL GINGIVAL GRAFT HARVESTING DEVICE

(71) Applicant: KING SAUD UNIVERSITY, Riyadh (SA)

(72) Inventor: Mansour Hamad Al Askar, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 17/019,160

(22) Filed: Sep. 11, 2020

(65) Prior Publication Data
US 2023/0320749 A1 Oct. 12, 2023

(51) Int. Cl.
*A61B 17/322* (2006.01)
*A61B 17/00* (2006.01)
*A61B 17/32* (2006.01)
*A61C 3/02* (2006.01)

(52) U.S. Cl.
CPC ............ *A61B 17/322* (2013.01); *A61C 3/02* (2013.01); *A61B 2017/00969* (2013.01); *A61B 2017/320064* (2013.01)

(58) Field of Classification Search
CPC . A61B 2017/505; A61B 17/322; A61B 17/50; A45D 26/0066; B25B 9/02; A61C 3/10
See application file for complete search history.

(56) References Cited

U.S. PATENT DOCUMENTS

| 2,652,832 A | * | 9/1953 | Castroviejo | A61B 17/2833 606/147 |
| 2,665,692 A |   | 1/1954 | L'Esperance |   |
| 4,593,693 A |   | 6/1986 | Schenck |   |
| 4,610,252 A |   | 9/1986 | Catalano |   |
| 4,821,718 A |   | 4/1989 | Uldall |   |
| 5,752,960 A | * | 5/1998 | Nallakrishnan | A61F 2/1664 606/107 |
| 5,997,567 A | * | 12/1999 | Cangelosi | A61B 17/04 294/99.2 |
| 8,608,774 B1 | * | 12/2013 | Alshemari | A61B 17/30 606/210 |

(Continued)

FOREIGN PATENT DOCUMENTS

CN 201153954 Y 11/2008
CN 103584899 A 2/2014
(Continued)

*Primary Examiner* — Sarah A Long
(74) *Attorney, Agent, or Firm* — Nath, Goldberg & Meyer; Richard C. Litman

(57) ABSTRACT

The palatal gingival graft harvesting device is a gripping tool for holding and manipulating palatal gingival grafts. The palatal gingival graft harvesting device includes a first arm having opposed first and second ends, and a second arm also having opposed first and second ends. The first arm and the second arm are pivotally joined to one another at a pivot joint adjacent the second ends thereof. The first end of the second arm has an opening formed therein for receiving a tip of the first end of the first arm. First and second bifurcated, U-shaped gripping jaws extend orthogonally from the second ends of the first and second arms. Central portions of the first and second arms are selectively and releasably lockable to one another to clamp the graft between the gripping jaws.

3 Claims, 5 Drawing Sheets

(56) References Cited

U.S. PATENT DOCUMENTS

2011/0151406 A1* 6/2011 Solano .................. A61C 19/05
433/162
2012/0303049 A1* 11/2012 Nakamura ......... A61B 17/3201
606/167

FOREIGN PATENT DOCUMENTS

| CN | 203634233 U | 6/2014 | |
|---|---|---|---|
| GB | 2433047 A | 6/2007 | |
| WO | 2004064871 A2 | 8/2004 | |
| WO | WO-2019224196 A1 * | 11/2019 | ............. A61B 17/30 |

* cited by examiner

PALATAL GINGIVAL GRAFT HARVESTING DEVICE

BACKGROUND

1. Field

The disclosure of the present patent application relates to surgical instruments, and particularly to a palatal gingival graft harvesting device with bifurcated gripping jaws for holding and manipulating a palatal gingival graft being harvested.

2. Description of the Related Art

Palatal gingival graft harvesting is used in connective tissue grafting procedures, which are relatively common procedures used in periodontics to increase the zone of keratinized tissue surrounding a tooth and a dental implant, to cover exposed roots, and to deepen the vestibule of a patient who has shallow vestibules. Keratinized tissue plays a major role around teeth and dental implants, aiding in maintaining and facilitating oral hygiene. Such grafting procedures are very delicate, and healing from such a gingival graft depends on many factors. A primary factor is the proper harvesting of the graft, where accuracy, time, minimal bleeding, and the secure transfer of the graft to the recipient site all depend on the harvesting procedure.

The harvesting process is particularly delicate and difficult because the hard palate, which is the donor site in a gingival graft procedure, has a lot of variation in thickness, along with some adipose tissue, as well as, in some cases, close proximity to the greater palatine artery. Without a proper tool for performing the palatal gingival graft harvesting procedure, it is difficult to harvest a gingival graft with an even overall thickness. Additional difficulties due to a lack of proper instrumentation may increase the overall surgical time, resulting in fatigue in the patient's temporomandibular joint, as well as risking damage to underlying tissue and vital anatomical landmarks.

Traditionally, palatal gingival graft harvesting is performed with conventional tweezers. However, tweezers are not delicate enough to overcome the above difficulties, resulting in not only additional time for the surgical procedure, but requiring multiple attempts to incise the graft from the donor side base, often resulting in excess bleeding. Additionally, due to the limited grasping surfaces of tweezers, a portion of the graft, typically along the border, is easily damaged, resulting in difficulties during the healing process.

An alternative technique involves the use of sutures to pull the graft, but this alternative technique is highly susceptible to tearing of the graft from the suture due to the uncontrolled force of the pulling, resulting in numerous attempts having to be made. A further alternative technique involves using a surgical blade and a surgical elevator instrument to release the graft from the bone. However, this results in lower overall quality of the graft, a thicker graft, and the inclusion of undesirable adipose tissue. A triangular or trapezoidal flap may also be surgically incised to harvest the graft, but this relatively large incision results in a great deal of bleeding due to the larger access opening. Thus, a palatal gingival graft harvesting device solving the aforementioned problems is desired.

SUMMARY

The palatal gingival graft harvesting device is a gripping tool for holding and manipulating palatal gingival grafts. The palatal gingival graft harvesting device includes a first arm having opposed first and second ends, and a second arm also having opposed first and second ends. The first arm and the second arm are pivotally joined to one another at a pivot joint adjacent the second ends thereof. The first end of the second arm has an opening formed therein for receiving the tip of the first end of the first arm.

First and second gripping jaws are mounted on the second ends of the first and second arms, respectively, and extend orthogonal to the first and second arms. Each of the first and second gripping jaws is bifurcated, having a central crossbar and a pair of tines mounted on opposite ends of the crossbar forming U-shaped jaws. The tines may extend orthogonal to the crossbar to form a substantially rectangular jaw. The gripping jaws pivot in such a manner that when the jaws are closed, the graft is gripped by the surface of the crossbars and the surfaces of the parallel tines, thereby providing a greater gripping surface area than the tip ends of the arms of conventional tweezers or forceps.

Central portions of the first and second arms are selectively and releasably lockable to one another. Although it should be understood that the central portions may be selectively and releasably locked using any suitable type of releasable locking or latching mechanism, in the present palatal gingival graft harvesting device, a first engaging member may be mounted on the central portion of the first arm, the first engaging member having a recess formed therein. A corresponding second engaging member may be mounted on the central portion of the second arm, the second engaging member having a protrusion or pin for releasable locking engagement with the recess of the first engaging member. It should be understood that, as an alternative, the first engaging member may be provided with the protrusion, and the second engaging member may be provided with the recess. The gripping jaws are normally open. The arms may be pressed together so that the jaws close and grip the graft, and the arms may be locked together by the above mechanism to clamp the graft between the jaws.

The central portions of the first and second arms may each have a convex curvature, and the central portions of the first and second arms are curved oppositely with respect to one another, such that each central portion is bowed outward. In use, as the user pinches the central portions towards one another, the first and second grasping jaws move toward one another, and as the user releases the central portions, such that they move apart, the first and second grasping jaws move apart.

These and other features of the present subject matter will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
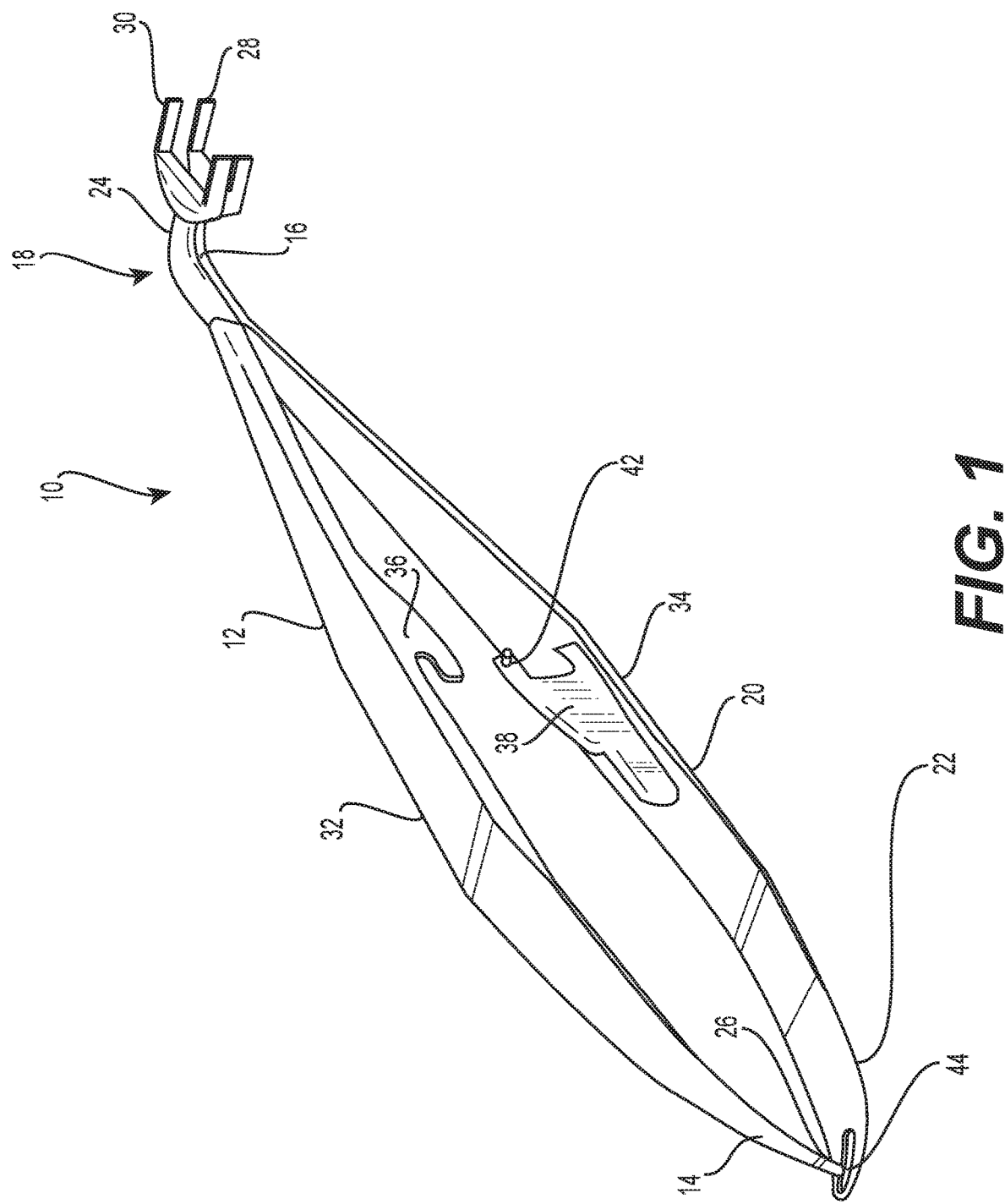
FIG. 1 is a front perspective view of a palatal gingival graft harvesting device.
Figure 2:
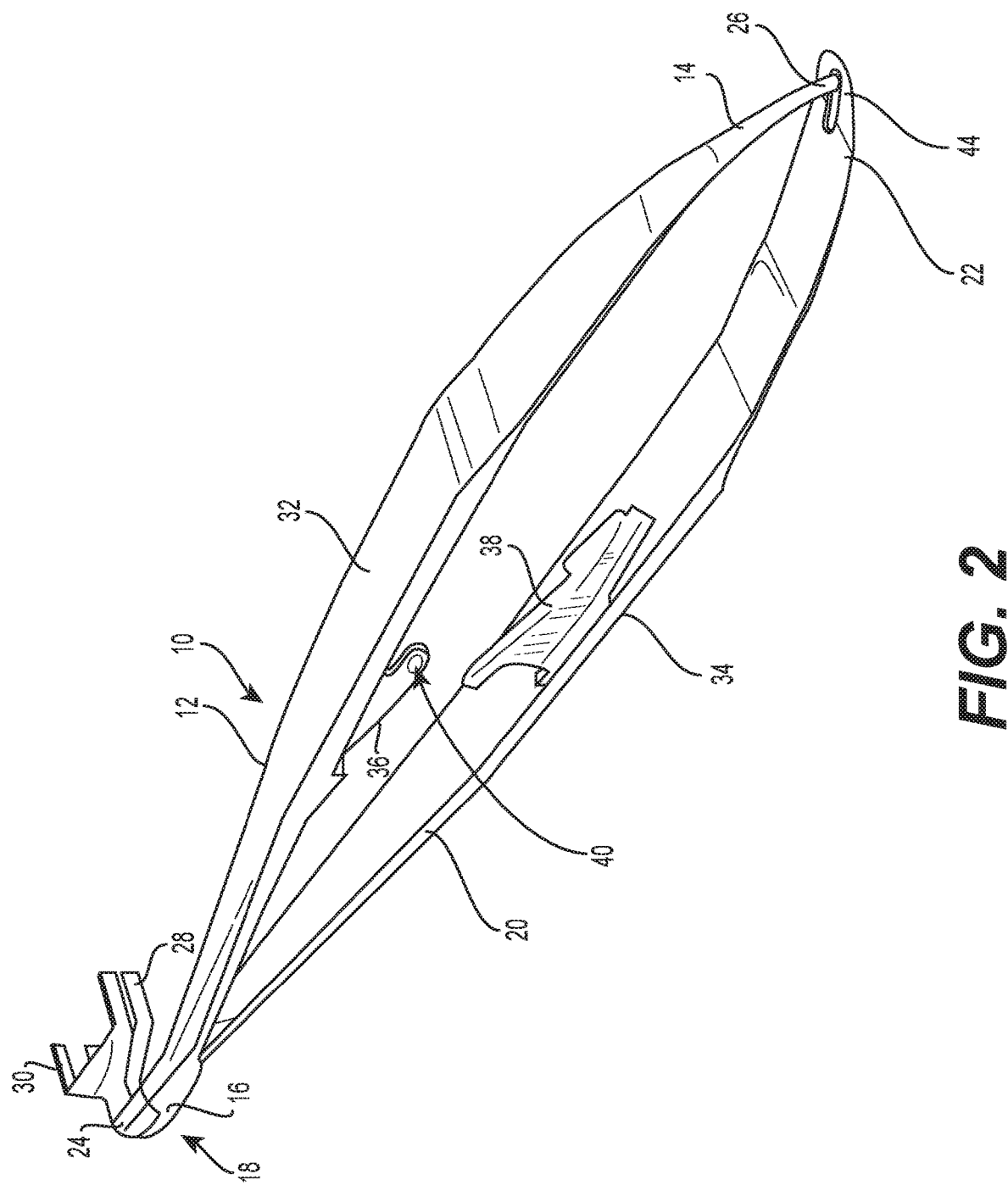
FIG. 2 is a rear perspective view of the palatal gingival graft harvesting device, shown with first and second grasping jaws thereof in an open position.
Figure 3:
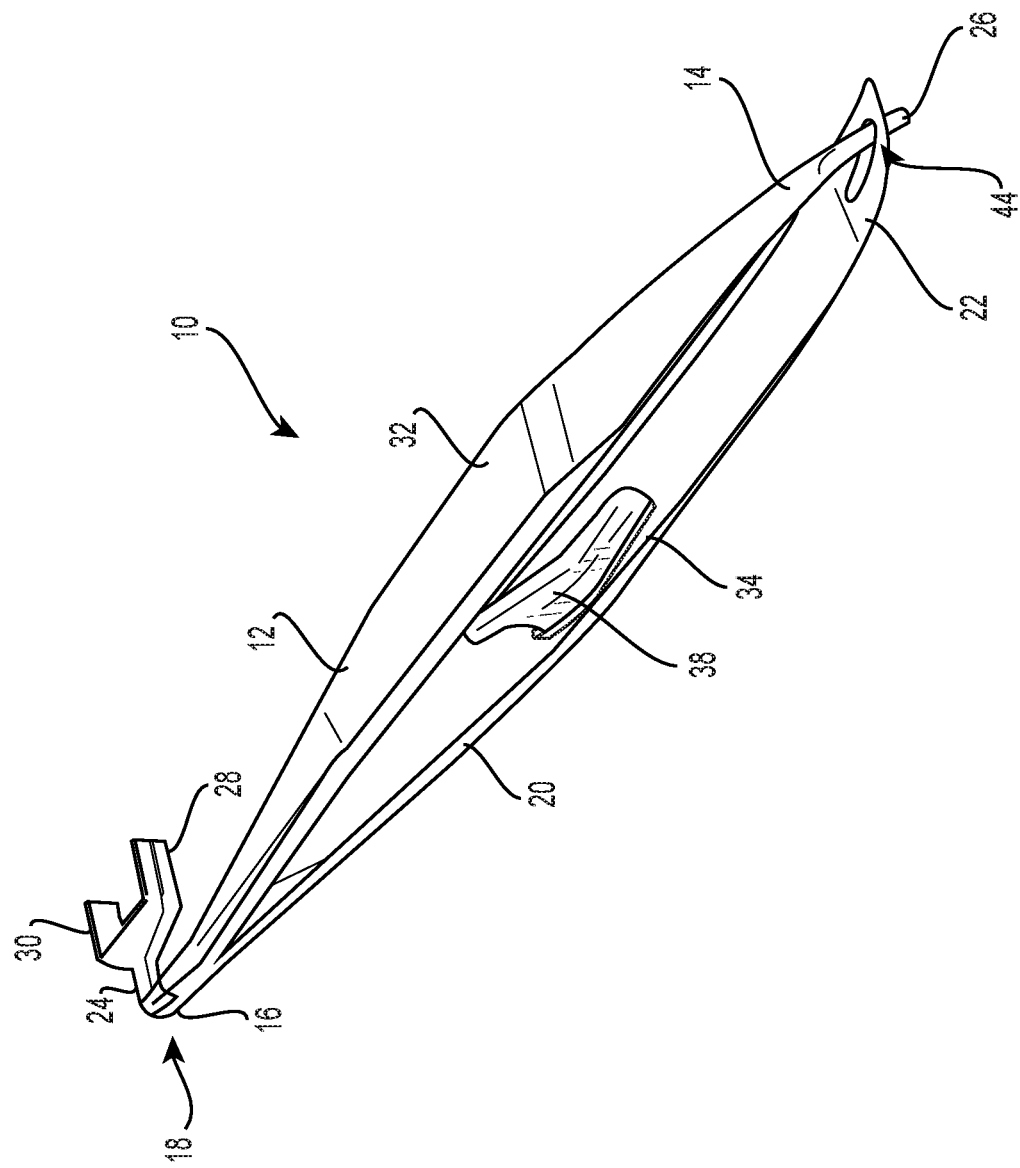
FIG. 3 is a rear perspective view of the palatal gingival graft harvesting device, shown with the first and second grasping jaws in a closed position.

The palatal gingival graft harvesting device 10 is a gripping tool for holding and manipulating palatal gingival grafts. As shown in FIGS. 1-3, the palatal gingival graft harvesting device 10 includes a first arm 12 having opposed first and second ends 14, 16, respectively, and a second arm 20 also having opposed first and second ends 22, 24, respectively. The first arm 12 and the second arm 20 are pivotally joined to one another at a pivot joint 18 adjacent the respective second ends 16, 24. The first end 22 of the second arm 20 has an opening 44 formed therein for receiving a tip 26 of the first end 14 of the first arm 12, which extends through the opening 44 when the arms 12 and 20 are compressed towards each other. It should be understood that although first and second arms 12, 20 are shown as having smooth surfaces, the first and second arms 12, 20 may include any suitable type of texturing, coating, serrations or the like for enhancing grasping by the user.

Figure 4:
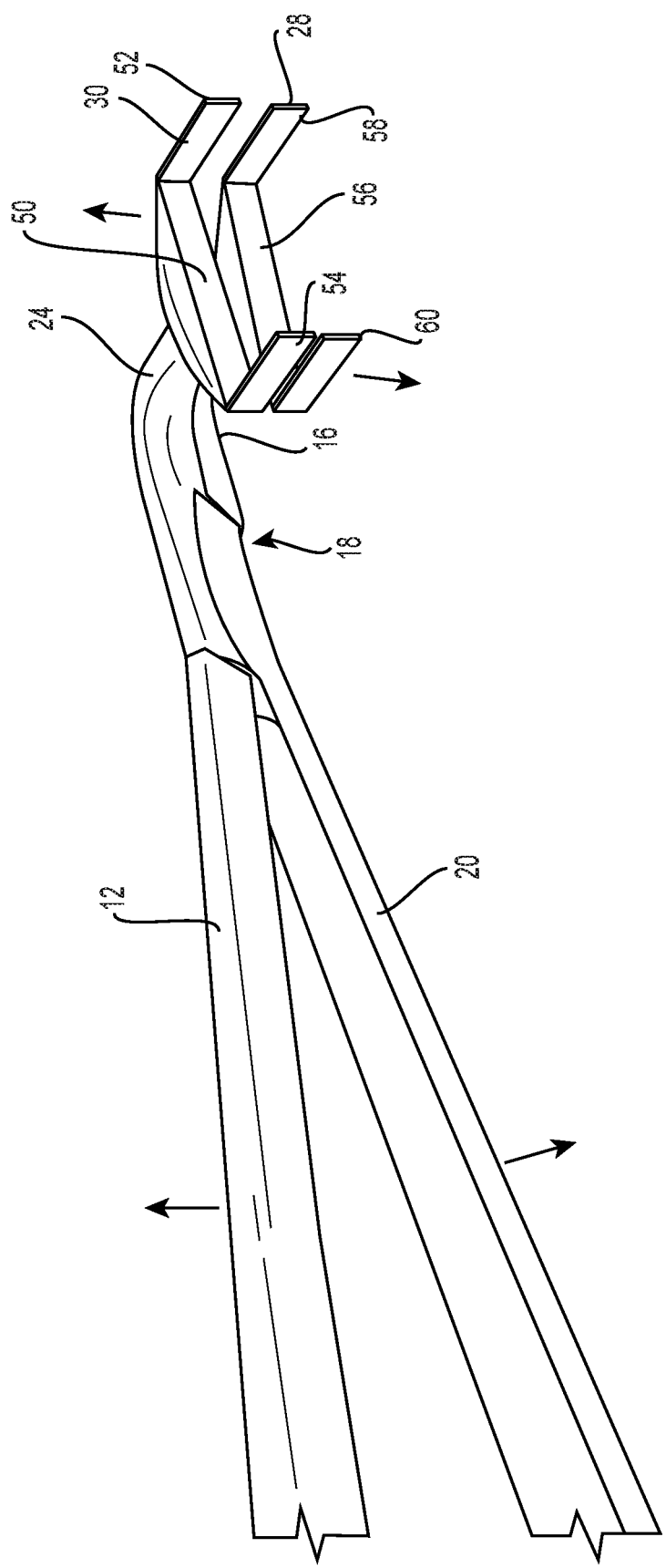
FIG. 4 is a partial front perspective view of the palatal gingival graft harvesting device, showing the first and second grasping jaws in the open position.
Figure 5:
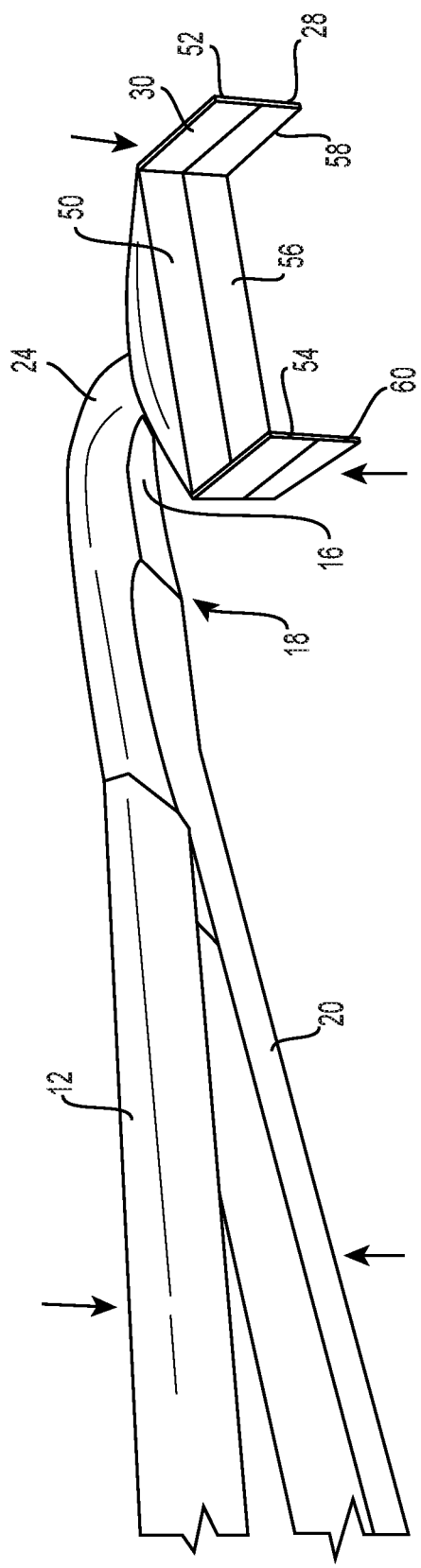
FIG. 5 is a partial front perspective view of the palatal gingival graft harvesting device, showing the first and second grasping jaws in the closed position.

As best seen in FIGS. 4 and 5, first and second gripping jaws 28, 30 are mounted on the second ends 16, 24 of the first and second arms 12, 20, respectively. It should be understood that the overall dimensions and configuration of the first and second gripping jaws 28, 30 are shown for exemplary purposes only. In FIGS. 4 and 5, the first gripping jaw 28 includes a central crossbar 56 and a pair of tines 58, 60 mounted on opposed ends of the crossbar 56. The pair of tines 58, 60 may extend orthogonally with respect to the central crossbar 56 to form a substantially U-shaped jaw. Similarly, the second grasping jaw 30 also includes a substantially identical central crossbar 50 and a substantially identical pair of tines 52, 54 mounted on opposed ends of the crossbar 50. The pair of tines 52, 54 may similarly extend orthogonally with respect to the crossbar 50 to form a substantially U-shaped jaw.

As exemplary dimensions, each of the first and second grasping jaws 28, 30 may have a thickness of approximately 3 mm, with a maximum separation between the first and second grasping jaws 28, 30 (in the open position) of approximately 4 mm. It should be noted that a typical palatal gingival graft being harvested has a thickness of approximately 1.5-2.0 mm. Each of the crossbars 50, 56 may have a length of approximately 15 mm, and each of the tines 52, 54, 58, 60 may have a length of approximately 7 mm.

Returning to FIGS. 1-3, central portions 32, 34 of the first and second arms 12, 20, respectively, are selectively and releasably lockable to one another. Although it should be understood that the central portions 32, 34 may be selectively and releasably locked using any suitable type of releasable locking or latching mechanism, in FIGS. 1-3, a first engaging member 36 is mounted on the central portion 32 of the first arm 12. As shown in FIG. 2, a recess 40 is formed in the engaging member 36. A corresponding second engaging member 38 is mounted on the central portion 34 of the second arm 20. The second engaging member 38 has a protrusion or pin 42 for releasable locking engagement with the recess 40 of the first engaging member 36. It should be understood that, as an alternative, the first engaging member 36 may be provided with the protrusion 42, and the second engaging member 38 may be provided with the recess 40. As a further alternative, more than one protrusion and more than one corresponding recess may be provided. Corresponding to the exemplary dimensions given above, the first engaging member 36 may have a length of approximately 3 mm and the second engaging member 38 may have a length of approximately 5 mm. The protrusion 42 may have a height of approximately 1.5 mm, and the recess 40 may have a corresponding depth.

At least the central portions 32, 34 of the first and second arms 12, 20 may each have a convex curvature. The central portions 32, 34 are curved oppositely with respect to one another, such that each of central portions 32, 34 is bowed outward, as shown. In use, as the user pinches the central portions 32, 34 towards one another (as indicated by the inward-facing arrows of FIG. 5), the first and second gripping jaws 28, 30 move toward one another, and as the user releases the central portions 32, 34, such that they move apart (as indicated by the outward-facing arrows of FIG. 4), the first and second gripping jaws 28, 30 move apart. As shown in FIG. 3, when the first and second gripping jaws 28, 30 are compressed towards each other, the user may lock the first and second gripping jaws 28, 30 in place through engagement between the first and second engaging members 36, 38, as described above. Further, as shown, as the user pinches the central portions 32, 34 towards one another, the first end 14 of first arm 12 moves further through opening 44 formed through the first end 22 of second arm 20. As central portions 32, 34 are released and move apart, the first end 14 of first arm 12 slides back, in the opposite direction, through opening 44.

As shown in FIGS. 4 and 5, the second ends 16, 24 of the first and second arms 12, 20 each have a flattened portion, the flattened portions overlapping and being connected by a pivot pin, which may be a rivet, screw, rod, or other short member so that the flattened portions slidably pivot across each other in a scissors movement as the arms are compressed towards each other and subsequently released. The flattened portions are followed by angle portions bent at approximately 90° angles so that the jaws 28, 30 extend orthogonal to the arms 12, 20. As the arms 12, 20 are compressed towards each other, the flattened portions pivot to more completely overlap each other, thereby approximating the jaws 28, 30 to grip the graft between the jaws 28, 30, and the arms 12, 20 may be locked by the locking mechanism to clamp the graft between the jaws 28, 30, if desired. The graft is gripped between the crossbars 50, 56 and between the two pairs of tines 52, 54 and 58, 60, providing a greater gripping surface area than conventional tweezers or forceps to grip the graft more securely. When the arms 12, 20 are unlocked and released, the flattened portions at the second ends 16, 24 pivot to decrease the overlapping area, thereby opening the jaws 28, 30 and releasing the graft.

It is to be understood that the palatal gingival graft harvesting device is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A palatal gingival graft harvesting device, comprising:
a first arm having opposed first and second ends, the first arm has a central portion wherein the first end of the first arm has a tapered tip configuration;
a second arm having opposed first and second ends, the second arm has a central portion, the first arm and the second arm each having overlapping flattened portions pivotally attached to one another at a pivot joint adjacent the second ends thereof, the first end of the second arm having an elongated opening formed therein receiving the tapered tip of the first end of the first arm thereby providing a sliding engagement therebetween;

a first bifurcated gripping jaw mounted on the second end of the first arm and extending orthogonally therefrom;

a second bifurcated gripping jaw mounted on the second end of the second arm and extending orthogonally therefrom parallel to the first bifurcated gripping jaw, the first and second bifurcated gripping jaws approximating each other in a closed position to grip a graft when the first and second arms are compressed towards each other and separating from each other in an open position when the first and second arms are released;

wherein each of the first and second bifurcated gripping jaws comprise:

a central crossbar having a first thickness; and a pair of tines mounted on opposite ends of the central crossbar, wherein the pair of tines extend orthogonal to the central crossbar and parallel to each other, defining bifurcated, U-shaped jaws, wherein the pair of tines are equal in thickness to the first thickness of the central crossbar such that a contact area formed from an inner surface of the U-shaped jaws is larger than a contact area formed between a lower surface of the first bifurcated gripping jaw and an upper surface of the second bifurcated gripping jaw when the first and second bifurcated gripping jaws are approximating each other in the closed position to grip the graft;

a first lock plate mounted on the central portion of the first arm, the first lock plate having a recess defined therein; and a second lock plate on the central portion of the second arm, the second lock plate having a protrusion for releasable locking engagement with the recess of the first lock plate.

2. The palatal gingival graft harvesting device as recited in claim 1, wherein the central portions of the first and second arms each have a convex curvature.

3. The palatal gingival graft harvesting device as recited in claim 2, wherein the central portions of the first and second arms are curved oppositely with respect to each other.

\* \* \* \* \*